(12) United States Patent
Ouchi

(10) Patent No.: US 7,387,632 B2
(45) Date of Patent: Jun. 17, 2008

(54) ENDOSCOPIC HIGH-FREQUENCY SNARE

(75) Inventor: Teruo Ouchi, Saitama (JP)

(73) Assignee: Hoya Corporation, Tokyo (JP)

( * ) Notice: Subject to any disclaimer, the term of this patent is extended or adjusted under 35 U.S.C. 154(b) by 634 days.

(21) Appl. No.: 10/986,763

(22) Filed: Nov. 15, 2004

(65) Prior Publication Data

US 2005/0131424 A1     Jun. 16, 2005

(30) Foreign Application Priority Data

Dec. 10, 2003   (JP)   ............... 2003-411373

(51) Int. Cl.
*A61B 18/18*  (2006.01)
(52) U.S. Cl. ..................... 606/47; 606/113
(58) Field of Classification Search ............ 606/45–47, 606/113, 114
See application file for complete search history.

(56) References Cited

U.S. PATENT DOCUMENTS

| | | | |
|---|---|---|---|
| 4,485,812 A |  | 12/1984 | Harada |
| 4,840,176 A |  | 6/1989 | Ohno |
| 5,437,665 A | * | 8/1995 | Munro ................. 606/47 |
| 6,224,611 B1 |  | 5/2001 | Ouchi |
| 6,245,078 B1 |  | 6/2001 | Ouchi |
| 6,506,209 B2 |  | 1/2003 | Ouchi |
| 6,944,490 B1 | * | 9/2005 | Chow ................. 600/374 |
| 7,115,125 B2 | * | 10/2006 | Nakao et al. ............ 606/47 |
| 7,270,663 B2 | * | 9/2007 | Nakao ................. 606/47 |

FOREIGN PATENT DOCUMENTS

| | | |
|---|---|---|
| JP | 7-8503 | 1/1995 |
| JP | 7-83749 | 9/1995 |
| JP | 2000-83963 | 3/2000 |

* cited by examiner

*Primary Examiner*—Michael Peffley
(74) *Attorney, Agent, or Firm*—Greenblum & Bernstein, P.L.C.

(57) ABSTRACT

A snare for an endoscope includes a flexible sheath, a control wire movable within the flexible sheath, and a snare loop connected to an end of the control wire, wherein when the control wire is axially advanced, the snare loop projects from the flexible sheath and expands into a loop shape, whereas when the control wire is axially retracted, the snare loop retracts into the flexible sheath and is folded into a closed shape. A resilient wire which forms the snare loop includes a hook portion protruding in a lateral direction of the snare loop. The resilient wire includes a biasing portion which biases the distal end of the resilient wire from a tip end to a base end of the hook portion to press the distal end of the resilient wire against an inner surface of the flexible sheath when the resilient wire is retracted.

8 Claims, 7 Drawing Sheets

ENDOSCOPIC HIGH-FREQUENCY SNARE

BACKGROUND OF THE INVENTION

1. Field of the Invention

The present invention relates to an endoscopic high-frequency snare for mucosal resection, and the like, via a passage of electric current through the snare, which is used by being introduced into a body through a treatment tool insertion channel of an endoscope.

2. Description of the Related Art

A typical endoscopic high-frequency snare is provided with an insulating flexible sheath, a conductive control wire which is inserted into the flexible sheath to be freely movable therein along the axis of the flexible sheath, and a snare loop made of a resilient wire which is fixed to the distal end of the control wire. The snare loop moves in and out of the distal end of the flexible sheath when the control wire is operated to retract and advance in the flexible sheath, respectively. The snare loop expands by its resiliency when positioned outside the flexible sheath, and becomes narrow when retracted into the flexible sheath. This type of endoscopic high-frequency snare is disclosed in, e.g., Japanese Patent Application Laid-open No.2000-83963.

In a typical endoscopic surgical operation for removing mucosa with an endoscopic high-frequency snare, firstly a mark or marks for indicating the area of a target affected part which is to be removed are made on a surface of the mucosa on the outline of the target affected part, subsequently the surface of the mucosa is dissected annularly along the mark or marks, and thereafter the target affected part of the mucosa surrounded by the annular cut is excised.

Among these three procedures, any conventional endoscopic high-frequency snare alone can perform only the procedure of excising mucosa such as the aforementioned target affected part of the mucosa surrounded by the annular cut. Namely, in addition to an endoscopic high-frequency snare, it is necessary to prepare a special marking tool, and another tool for dissecting mucosa. Therefore, each treatment tools, i.e., the endoscopic high-frequency snare, the marking tool and the dissecting tool, must be interchanged with another treatment tool thereof in order to be used, which makes the endoscopic surgical operation troublesome and complicated, and raises the possibility of contaminated water being scattered each time such treatment tools are interchanged; moreover, the disinfecting operation for the treatment tools becomes troublesome.

To prevent this problem from occurring, if the resilient wire that forms the snare loop is provided at a distal end of the resilient wire with a hook portion, which is formed by bending a portion of the resilient wire in the vicinity of the distal end thereof so that the hook portion projects in a lateral direction of the snare loop, both the aforementioned marking and mucosa dissection procedures can be carried out with the hook portion before the aforementioned mucosa excision procedure with the snare loop.

However, if such a hook portion is formed simply by bending a portion of the resilient wire of the snare loop laterally in the vicinity of the distal end thereof, there is a possibility of the hook portion largely protruding in a lateral direction (radial direction) of the flexible sheath from the distal end of the flexible sheath to such an extend as to get caught by an inner peripheral surface of a channel (e.g., treatment tool insertion channel) of an endoscope, thus making it difficult for the endoscopic high-frequency snare to travel in the channel or damaging the snare loop, when the endoscopic high-frequency snare is inserted and withdrawn into and from the channel.

SUMMARY OF THE INVENTION

The present invention provides an endoscopic high-frequency snare, with which the marking procedure, the mucosa dissection procedure and the mucosa excision procedure can be easily performed successively without the use of any other treatment tool, and which can travel smoothly in a channel of an endoscope when a mucosa is removed trans-endoscopically with the endoscopic high-frequency snare.

According to an aspect of the present invention, a snare for an endoscope is provided, including a flexible sheath, a control wire axially movable within the flexible sheath; and a snare loop connected to a distal end of the control wire, wherein when the control wire is axially advanced, the snare loop projects from a distal end of the flexible sheath and expands into a loop shape due to resiliency of the snare loop, whereas when the control wire is axially retracted, the snare loop retracts into the distal end of the flexible sheath and is folded into a closed shape. A resilient wire which forms the snare loop includes a hook portion at a distal end of the resilient wire, the hook portion protruding in a lateral direction of the snare loop. The resilient wire includes a biasing portion which biases the distal end of the resilient wire in a direction from a tip end to a base end of the hook portion to press the distal end of the resilient wire against an inner peripheral surface of the flexible sheath in a state where the resilient wire is retracted into the distal end of the flexible sheath.

It is desirable for the hook portion to be formed by bending a portion of the resilient wire in a vicinity of the distal end thereof so that the hook portion protrudes in the lateral direction of the snare loop.

It is desirable for the biasing portion to be formed by bending a portion of the resilient wire in a vicinity of the distal end of the resilient wire so that the biasing portion is resiliently in pressing contact with an inner peripheral surface of the flexible sheath to bias the distal end of the resilient wire in the direction from the tip end to the base end of the hook portion in a state where the resilient wire is retracted into the distal end of the flexible sheath.

It is desirable for the biasing portion to be formed by forming the resilient wire in an arc shape as a whole so that the biasing portion is resiliently in pressing contact with an inner peripheral surface of the flexible sheath to bias the distal end of the resilient wire in the direction from the tip end to the base end of the hook portion in a state where the resilient wire is retracted into the distal end of the flexible sheath.

It is desirable for a length of the hook portion to be determined so that the tip end of the hook portion is positioned in a close vicinity of an outer edge of the flexible sheath in a state where the resilient wire is retracted into the distal end of the flexible sheath.

It is desirable for the flexible sheath and the control cable to be made of an insulating material and a conductive material, respectively.

It is desirable for the length of the hook portion to substantially correspond to an outside diameter of the flexible sheath minus a wall thickness of the flexible sheath.

It is desirable for the resilient wire to include two resilient wires extending between two mutually secured portions, wherein the hook portion and the biasing portion are formed on one and the other of the two resilient wires, respectively.

The hook portion can be formed by bending the portion of the resilient wire in a substantially L shape.

In another embodiment, a snare for an endoscope is provided, including a flexible sheath; a control wire axially movable within the flexible sheath; a snare loop made of at least one resilient wire and fixed to a distal end of the control wire, the snare loop expanding and becoming narrow when the control wire is advanced and retracted to make the snare loop project and retract from and into a distal end of the flexible sheath, respectively; a hook portion formed on the resilient wire at a distal end thereof; and a biasing portion, formed on the resilient wire between the hook portion and another end of the resilient wire which is connected to the distal end of the control wire, for biasing the distal end of the resilient wire in a direction from a tip end to a base end of the hook portion to press the distal end of the resilient wire against an inner peripheral surface of the flexible sheath in a state where the resilient wire is retracted into the distal end of the flexible sheath.

The present disclosure relates to subject matter contained in Japanese Patent Application No. 2003-411373 (filed on Dec. 10, 2003) which is expressly incorporated herein by reference in its entirety.

BRIEF DESCRIPTION OF THE DRAWINGS

The present invention will be discussed below in detail with reference to the accompanying drawings, in which.

DESCRIPTION OF THE PREFERRED EMBODIMENTS

Figure 1:
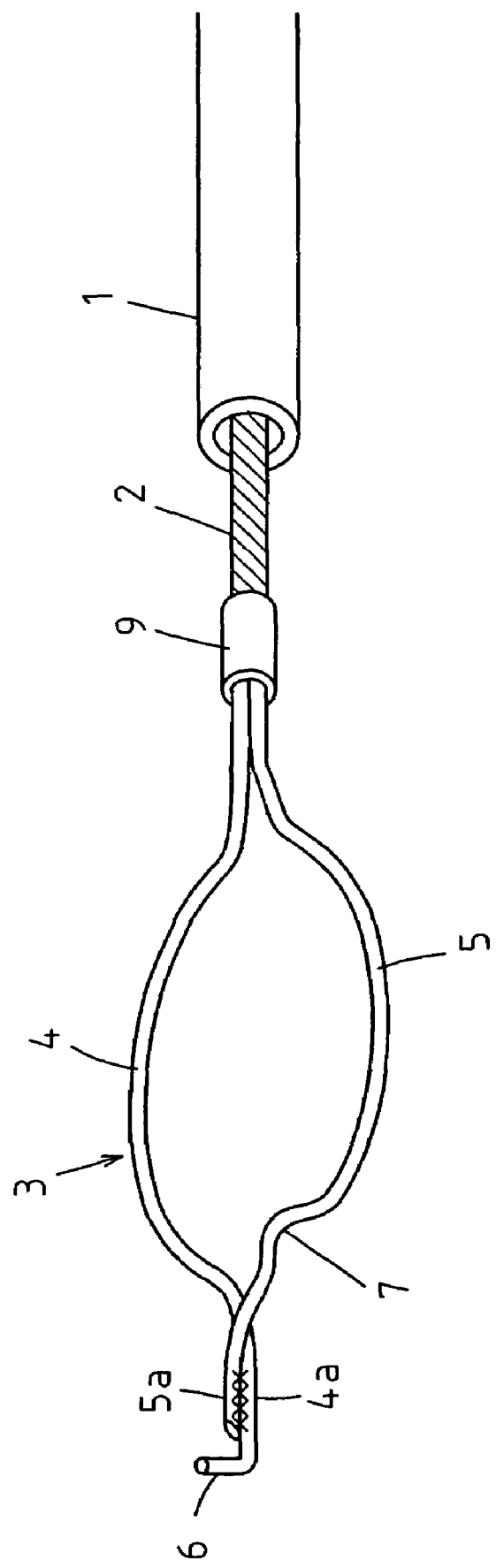
FIG. 1 is a perspective view of a first embodiment of an endoscopic high-frequency snare according to the present invention, showing a state where a snare loop formed at the distal end of the endoscopic high-frequency snare expands by its resiliency when positioned outside a distal end of flexible sheath.
Figure 2:
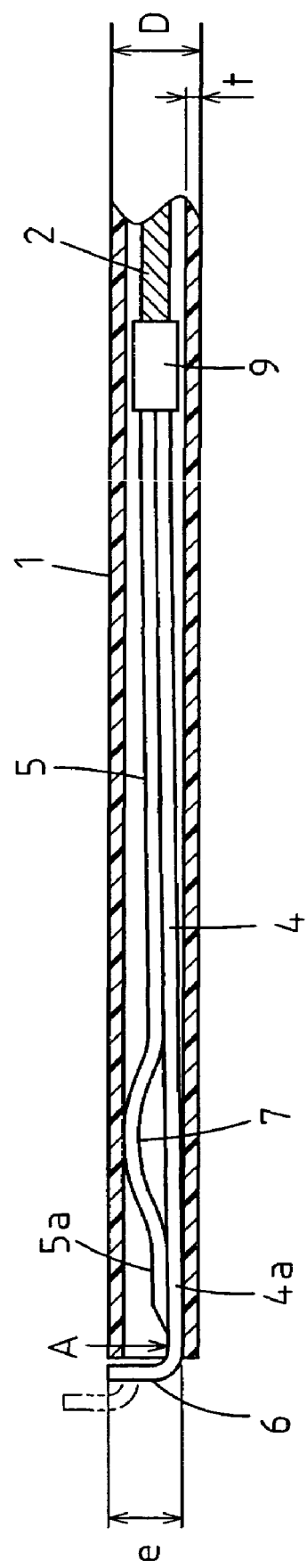
FIG. 2 is a longitudinal sectional view of the endoscopic high-frequency snare shown in FIG. 1, showing a state where the snare loop becomes narrow when withdrawn into the distal end of the flexible sheath.

FIGS. 1 and 2 show a distal end portion of a first embodiment of an endoscopic high-frequency snare according to the present invention. FIG. 1 shows a state where a snare loop 3 formed at the distal end of the endoscopic high-frequency snare expands by its resiliency when positioned outside a distal end of a flexible sheath 1, and FIG. 2 shows a state where the snare loop 3 becomes narrow when withdrawn into the distal end of the flexible sheath 1.

The first embodiment of the endoscopic high-frequency snare is provided with the aforementioned flexible sheath 1, a control wire 2 and a snare loop 3. In this particular embodiment of the endoscopic high-frequency snare, the flexible sheath 1 is formed from an insulating flexible tube such as a tetrafluoroethylene resin tube, while the control wire 2 is formed from an electrically conductive flexible wire such as a stranded stainless steel wire.

The snare loop 3 is formed by a pair of electrically conductive resilient wires 4 and 5. The rear ends of the pair of resilient wires 4 and 5 are fixed to each other and joined to the distal end of the control wire 2 via a metal connection pipe 9. The control wire 2 is axially movably inserted in the flexible sheath 1. The control wire 2 is actuated to advance or retract as desired at a control portion (not shown) connected to the proximal end (not shown) of the flexible sheath 1, so that the snare loop 3 moves in and out of the distal end of the flexible sheath 1 when the control wire 2 is operated to retract and advance axially, respectively, in the flexible sheath 1.

When the snare loop 3 is positioned outside the flexible sheath 1 in a state where no external force is applied thereto, the snare loop 3 forms a curved loop by its resiliency as shown in FIG. 1. The snare loop 3 is deformed resiliently to become narrow when drawn into the flexible sheath 1 as shown in FIG. 2.

Since each of the pair of resilient wires 4 and 5 form the snare loop 3, for example, a single or stranded stainless steel wire can be used. A high-frequency electric current can be supplied to the snare loop 3 through the control wire 2.

Rear ends of the pair of resilient wires 4 and 5 are positioned side by side in the connection pipe 9, while front ends of the pair of resilient wires 4 and 5 are positioned side by side and joined to each other by a known fixing method such as silver brazing, gold brazing or laser spot welding.

One of the pair of resilient wires 4 and 5, specifically the resilient wire 4 in this particular embodiment, is provided at a distal end thereof with a hook portion 6 which is formed by bending a portion of the resilient wire 4 in the vicinity of the distal end thereof in a substantially L shape so that the hook portion 6 protrudes in a lateral direction of the snare loop 3 (upwards as viewed in FIG. 1). The length of the hook portion 6 (shown by "e" in FIG. 2: a length from a bottom (side) surface of the resilient wire 4 to the upper end of the hook portion 6 as viewed in FIG. 2) is set to a length substantially equal to an outside diameter D (shown in FIG. 2) of the flexible sheath 1 minus a wall thickness t (shown in FIG. 2) of the flexible sheath 1, i.e., e≈D−t.

By determining the length of the hook portion 6 in this manner, the length of the hook portion 6 can be provided as long as possible so as to be easily engaged with a streak fiber tissue of a mucosa, or the like, to resect the same with a high-frequency current.

The other of the pair of resilient wires 4 and 5, specifically the resilient wire 5 in this particular embodiment, is provided in the vicinity of the distal thereof with a biasing portion (bend portion) 7, which is shaped to bias the joined distal ends of the pair of resilient wires 4 and 5 in a direction (shown by an arrow A in FIG. 2) from the tip end to the base end (from the upper end to the lower end as viewed in FIG. 2) of the hook portion 6 to press the joined distal ends of the pair of resilient wires 4 and 5 against an inner peripheral surface of the flexible sheath 1 when the pair of resilient wires 4 and 5 that form the snare loop 3 are positioned inside the flexible sheath 1.

The biasing portion 7 is formed by bending a portion of the resilient wire 5, in the vicinity of the distal end thereof, so as to protrude in a direction generally parallel to the protruding direction of the hook portion 6 as shown in FIG. 2, with the snare loop 3 retracted into the flexible sheath 1. In the state shown in FIG. 2, the biasing portion 7 is resiliently in pressing contact with an inner peripheral surface of the flexible sheath 1 to bias the joined distal ends of the pair of resilient wires 4 and 5 in a lateral direction thereof (downwards as viewed in FIG. 2), thereby pressing at least a portion of the resilient wire 4, in the close vicinity of the base end (lower end as viewed in FIG. 2) of the hook portion 6, against an inner peripheral surface of the flexible sheath 1 that is opposite to the inner peripheral surface of the flexible sheath 1 to which the biasing portion 7 is in pressing contact with.

Due to such a structure, the tip of the hook portion 6 is positioned immediately in front of the distal end of the flexible sheath 1 in the close vicinity of an outer edge (upper edge as viewed in FIG. 2) of the flexible sheath 1 in a state shown in FIG. 2 where the pair of resilient wires 4 and 5 are retracted into the distal end of the flexible sheath 1, and accordingly the hook portion 6 is not positioned to largely protrude in a lateral direction of the flexible sheath 1 from on outer edge thereof as shown by a two-dot chain line in FIG. 2. Consequently, there is little possibility of the hook portion 6 getting snagged on an inner peripheral surface of a channel (e.g., a treatment tool insertion channel) of an endoscope, so that the flexible sheath 1 can be made to pass through the channel smoothly.

Figure 3:
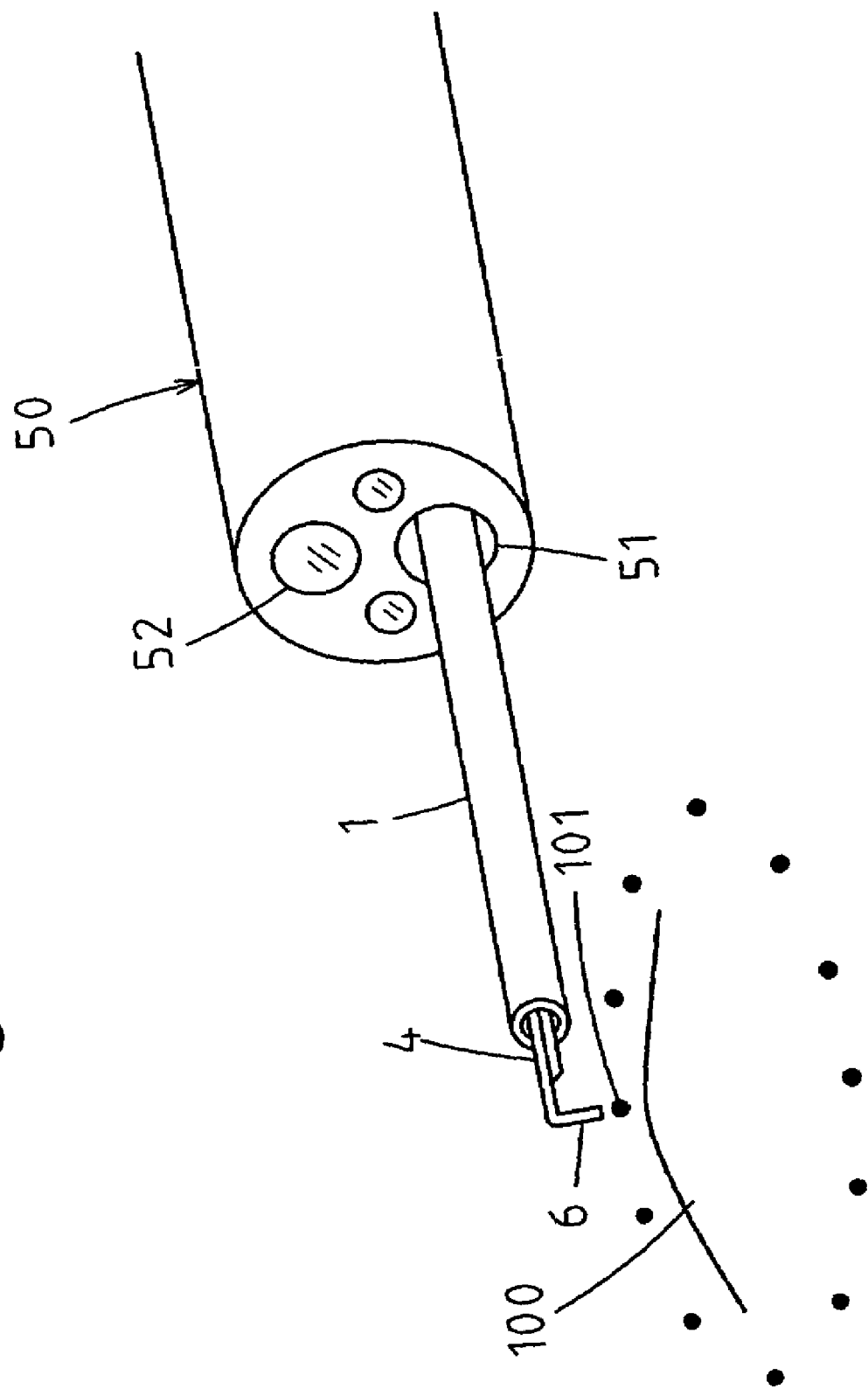
FIG. 3 is a perspective view of a distal end of an insertion tube of an endoscope from which the distal end of the endoscopic high-frequency snare shown in FIGS. 1 and 2 protrudes, and a target affected part of a mucosa, around which spot marks are made with the first embodiment of the endoscopic high-frequency snare.

As shown in FIG. 3, the first embodiment of the endoscopic high-frequency snare that has the above described arrangement is inserted into a treatment tool insertion channel 51 of an insertion tube of an endoscope 50 to make the distal end of the endoscopic high-frequency snare extend out of the distal end (open end) of the treatment tool insertion channel 51 to be capable of performing a marking procedure, mucosa dissection procedure and a mucosa excision procedure successively, while the distal end of the endoscopic high-frequency snare is seen through an objective window 52 located at the distal end of the insertion tube of the endoscope 50.

FIG. 3 shows a state where a plurality of spot marks 101 are made on a surface of a mucosa around a target affected part 100 thereof with the use of the first embodiment of the endoscopic high-frequency snare. Each spot mark 101 is made as a burn mark by passing a high frequency current through the snare loop 3 for a short period of time with the tip of the hook portion 6 contacting a surface of the mucosa on the periphery of the target affected part 100.

Figure 4:
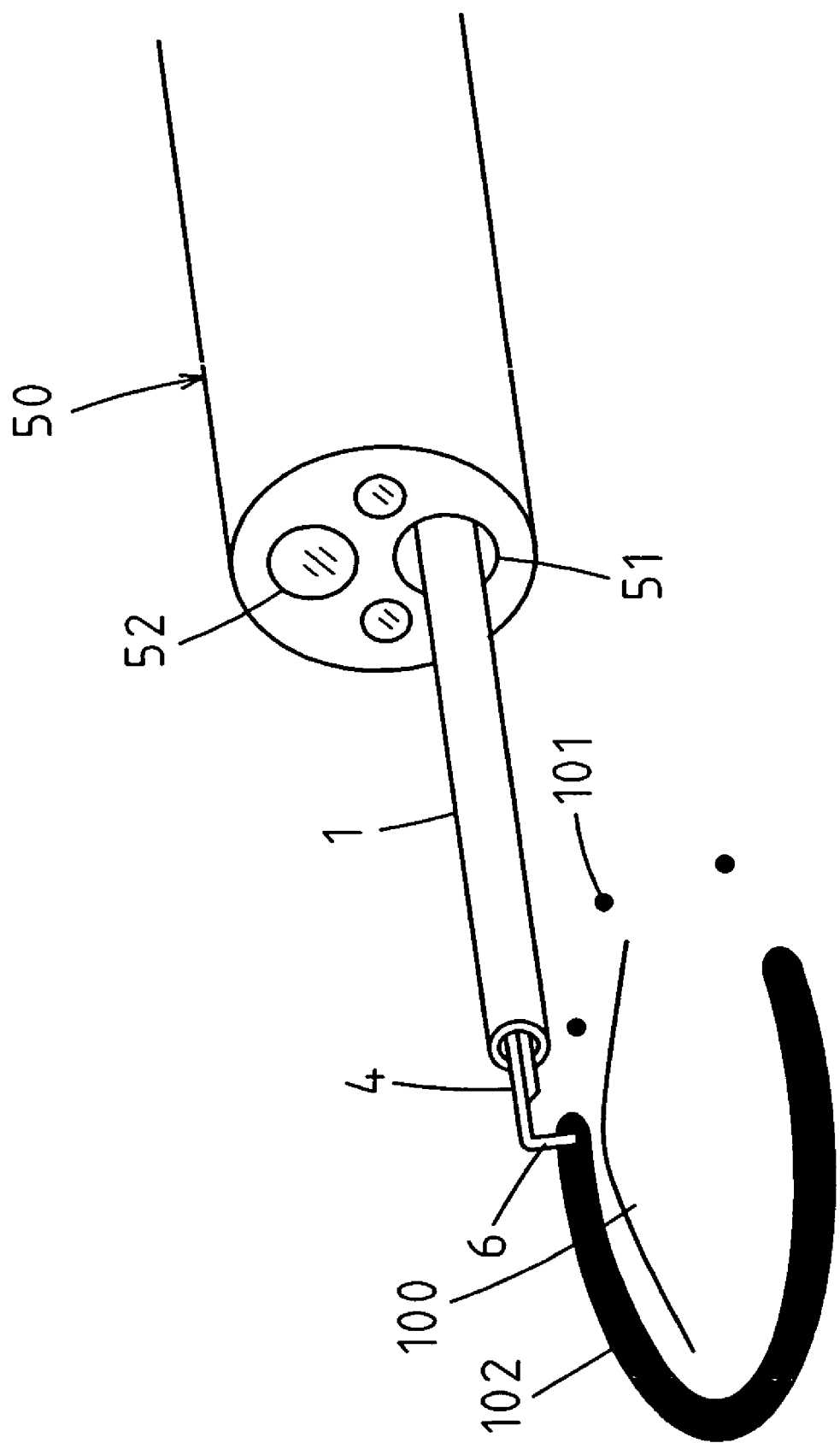
FIG. 4 is a view similar to that of FIG. 3, showing a mucosa dissection procedure with the first embodiment of the endoscopic high-frequency snare.
Figure 5:
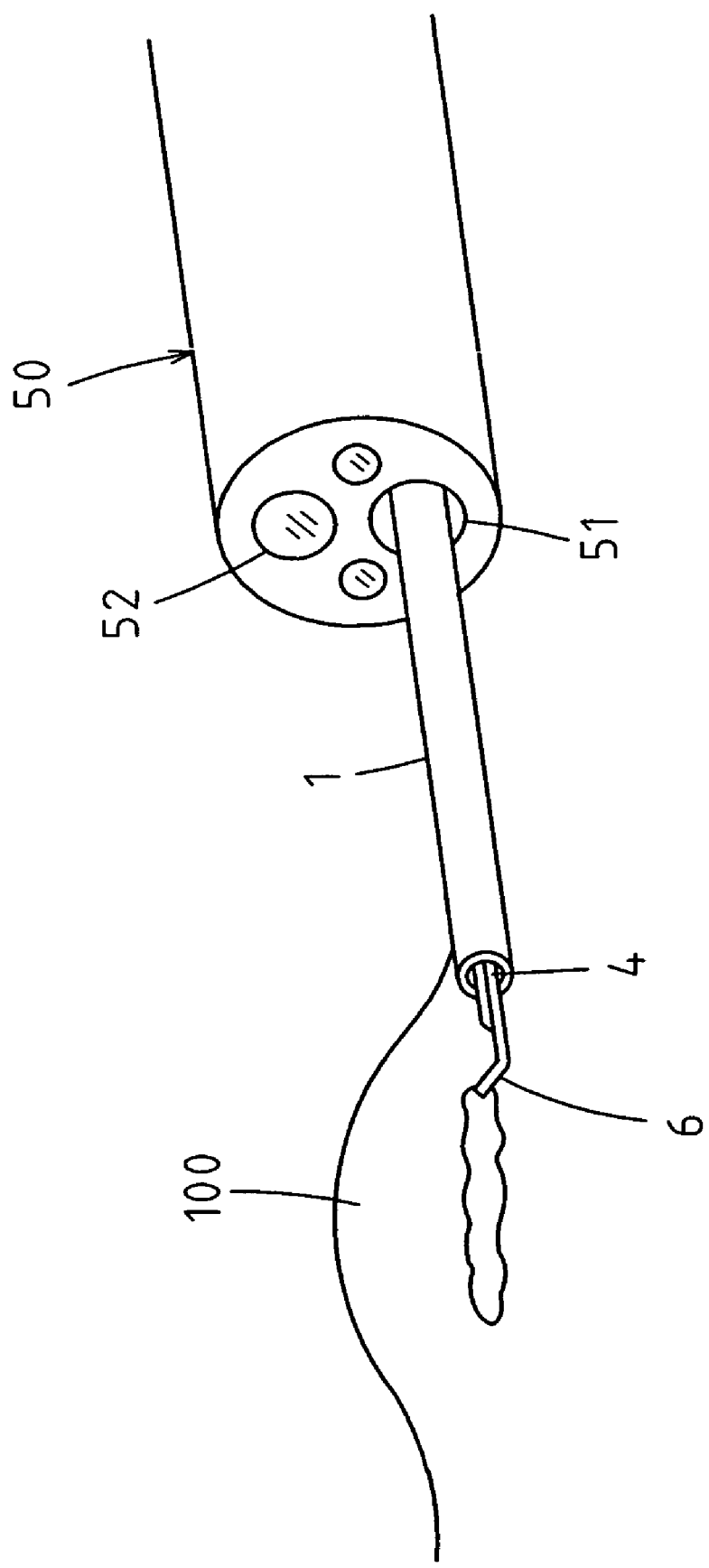
FIG. 5 is a view similar to that of FIG. 3, showing another mucosa dissection procedure with the first embodiment of the endoscopic high-frequency snare.

FIG. 4 shows a mucosa dissection procedure with the first embodiment of the endoscopic high-frequency snare, which is carried out after completion of the marking procedure shown in FIG. 3. The mucosa is dissected along the outline of the target affected part 100 by moving the hook portion 6 while penetrating into the mucosa and passing a high frequency current through the snare loop 3 in a manner so that the hook portion 6 traces the spot marks 101. It is also possible for a side surface of the target affected part 100 be dissected easily with the first embodiment of the endoscopic high-frequency snare in a manner shown in FIG. 5.

Figure 6:
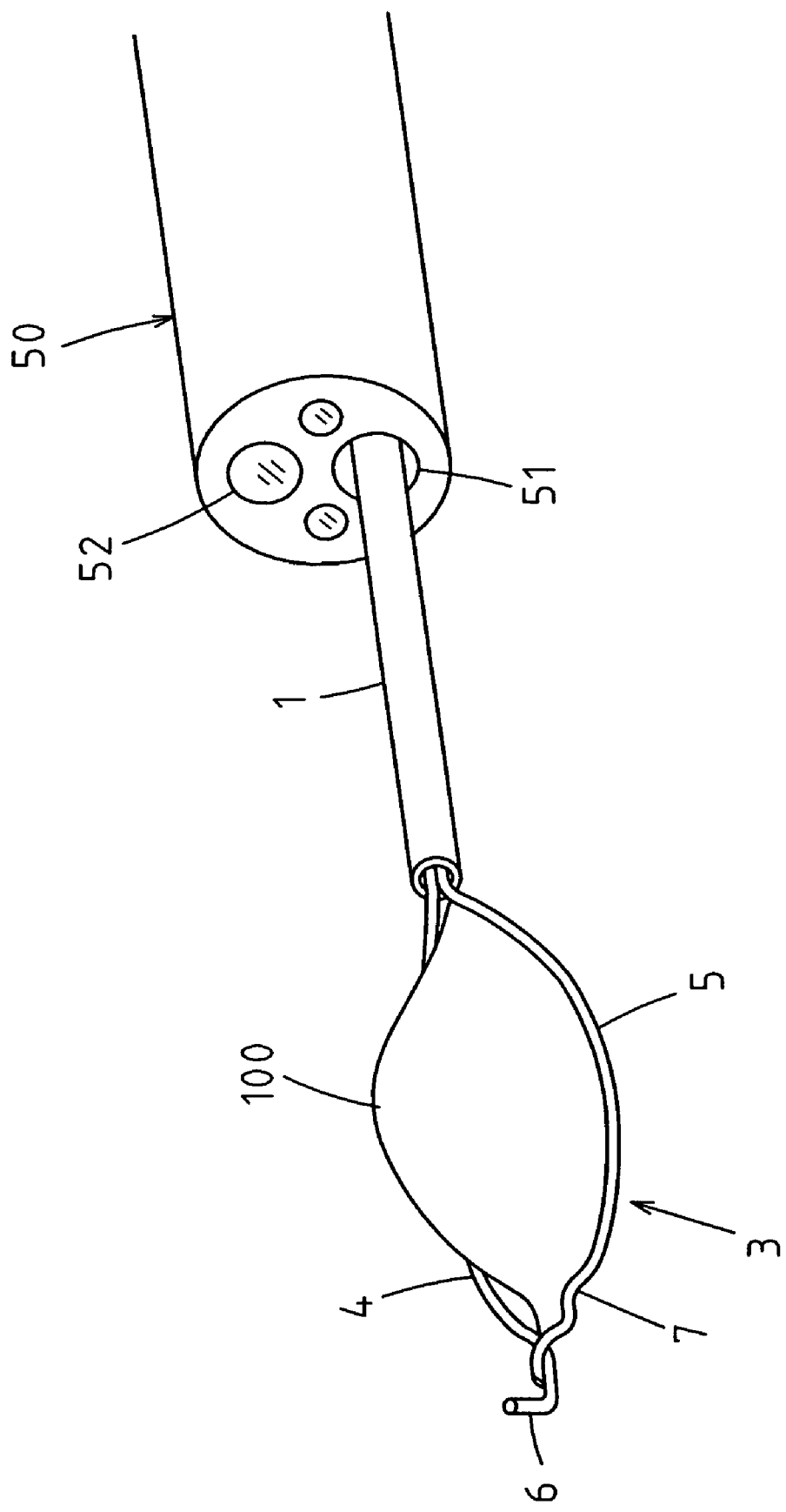
FIG. 6 is a view similar to that of FIG. 3, showing a mucosa excision procedure with the first embodiment of the endoscopic high-frequency snare.

FIG. 6 shows a mucosa excision procedure with the first embodiment of the endoscopic high-frequency snare, which is carried out lastly. The target affected part 100 can be excised easily by firstly surrounding the target affected part 100 (the mucosa of which on the outer edge of the target affected part 100 has been dissected) with the snare loop 3 and subsequently passing a high frequency current through the snare loop 3 while gradually narrowing the snare loop 3 by retracting the snare loop 3 into the flexible sheath 1.

The present invention is not limited solely to the above described particular embodiment. Although the biasing portion 7 is formed on the resilient wire 5, on which the hook portion 6 is not formed, in the above illustrated embodiment of the endoscopic high-frequency snare, the biasing portion 7 can be formed on the other resilient wire 4, on which the hook portion 6 is formed, rather than on the resilient wire 5.

Figure 7:
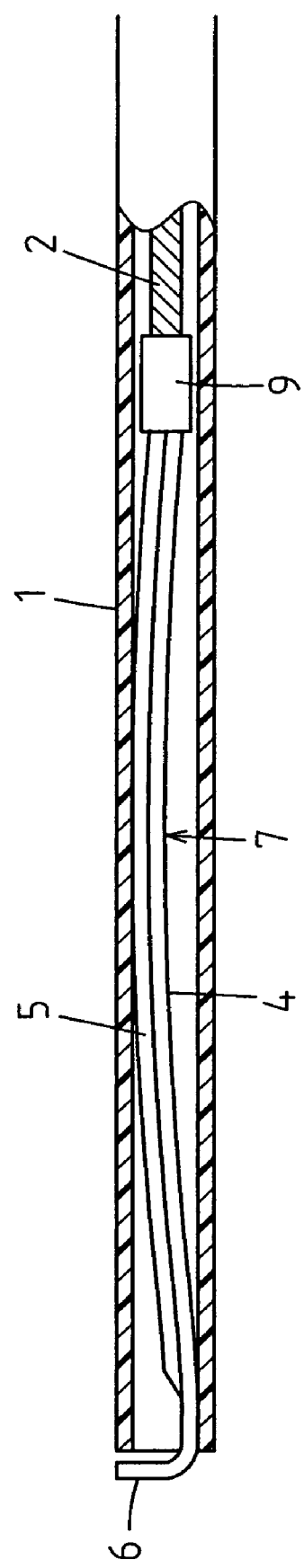
FIG. 7 is a longitudinal sectional view of a second embodiment of the endoscopic high-frequency snare, showing a state where the snare loop becomes narrow when withdrawn into the distal end of the flexible sheath.

Additionally, a biasing portion corresponding to the biasing portion 7 can be formed on the snare loop 3 by forming one or each of the pair of resilient wires 4 and 5 in an arc shape as a whole as shown in FIG. 7. In this case, the biasing portion corresponding to the biasing portion 7 only needs to be pressed against an inner peripheral surface of the flexible sheath to be deformed resiliently so that a small portion of the snare portion 3 in the close vicinity of the base end of the hook portion 6 is pressed against an inner peripheral surface of the flexible sheath 1 that is opposite to the inner peripheral surface of the flexible sheath 1 to which this biasing portion is in pressing contact with.

According to the present invention, firstly the marking procedure and the mucosa dissection procedure, and subsequently the mucosa excision procedure, can be carried out with the endoscopic high-frequency snare by virtue of the hook portion that is provided at a distal end of the resilient wire and protrudes in a lateral direction of the snare loop. Accordingly, the marking procedure, the mucosa dissection procedure and the mucosa excision procedure can be easily performed successively with a single treatment tool, i.e., the endoscopic high-frequency snare according to the present invention. Moreover, since the biasing portion, which biases the distal end of the resilient wire in a direction from the tip end to the base end of the hook portion (to press the distal end of the resilient wire against an inner peripheral surface of the flexible sheath in a state where the resilient wire is retracted into the distal end of the flexible sheath), is formed on the resilient wire, the endoscopic high-frequency snare can travel smoothly in a channel of an endoscope.

Obvious changes may be made in the specific embodiments of the present invention described herein, such 20 modifications being within the spirit and scope of the invention claimed. It is indicated that all matter contained herein is illustrative and does not limit the scope of the present invention.

What is claimed is:

1. A snare for an endoscope, comprising:
a flexible sheath;
a control wire configured to move axially within said flexible sheath; and
a snare loop connected to a distal end of said control wire, wherein when said control wire is axially advanced, said snare loop projects from a distal end of said flexible sheath and expands into a loop shape due to resiliency of said snare loop, and when said control wire is axially retracted, said snare loop retracts into said distal end of said flexible sheath and is folded into a closed shape,
wherein a resilient wire which forms said snare loop includes a hook portion at a distal end of said resilient wire, said hook portion protruding in a lateral direction of said snare loop, wherein a length of said hook portion is configured such that a tip end of said hook portion is positioned in close proximity to an outer edge of said flexible sheath when said resilient wire is retracted into said distal end of said flexible sheath, wherein said length of said hook portion substantially corresponds to an outside diameter of said flexible sheath minus a wall thickness of said flexible sheath, and wherein said resilient wire includes a biasing portion which biases said distal end of said resilient wire in a biasing direction, extending from said tip end to a base end of said hook portion, such that said distal end of said resilient wire is pressed against an inner peripheral surface of said flexible sheath when said resilient wire is retracted into said distal end of said flexible sheath.

2. The snare according to claim 1, wherein said hook portion is formed by bending a portion of said resilient wire in a vicinity of said distal end thereof so that said hook portion protrudes in said lateral direction of the snare loop.

3. The snare according to claim 1, wherein said biasing portion is formed by bending a portion of said resilient wire in a vicinity of said distal end of said resilient wire so that said biasing portion is configured to resiliently and pressingly contact an inner peripheral surface of said flexible sheath to bias said distal end of said resilient wire in said biasing direction when said resilient wire is retracted into said distal end of said flexible sheath.

4. The snare according to claim 1, wherein said biasing portion is formed by forming said resilient wire in an arc shape so that said biasing portion is configured to resiliently and pressingly contact an inner peripheral surface of said flexible sheath to bias said distal end of said resilient wire in said biasing direction when said resilient wire is retracted into said distal end of said flexible sheath.

5. The snare according to claim 1, wherein said flexible sheath and said control cable comprise an insulating material and a conductive material, respectively.

6. The snare according to claim 1, wherein said resilient wire comprises two resilient wires extending between two secured portions, wherein said hook portion and said biasing portion are formed on one and the other of said two resilient wires, respectively.

7. The snare according to claim 2, wherein said hook portion is formed by bending said portion of said resilient wire in a substantially L shape.

8. A snare for an endoscope, comprising:

a flexible sheath;

a control wire axially movable within said flexible sheath;

a snare loop comprising at least one resilient wire and fixed to a distal end of said control wire, said snare loop configured to expand and narrow when said control wire is advanced and retracted such that said snare loop projects and retracts from and into a distal end of said flexible sheath, respectively;

a hook portion formed on said resilient wire at a distal end thereof; and a biasing portion, formed on said resilient wire between said hook portion and another end of said resilient wire which is connected to said distal end of said control wire, for biasing said distal end of said resilient wire in a biasing direction extending from a tip end to a base end of said hook portion, the biasing portion being configured to press said distal end of said resilient wire against an inner peripheral surface of said flexible sheath when said resilient wire is retracted into said distal end of said flexible sheath, wherein a length of said hook portion is configured such that said tip end is positioned in close proximity to an outer edge of said flexible sheath when said resilient wire is retracted into said distal end of said flexible sheath, and wherein said length of said hook portion substantially corresponds to an outside diameter of said flexible sheath minus a wall thickness of said flexible sheath.

* * * * *